United States Patent
Zheng et al.

(10) Patent No.: US 9,365,596 B2
(45) Date of Patent: Jun. 14, 2016

(54) METHOD FOR PREPARING QUATERNARY PHOSPHONIUM SALTS

(71) Applicant: Microvast Power Systems Co.,Ltd., Huzhou (CN)

(72) Inventors: Zhuoqun Zheng, Huzhou (CN); Dawei Shen, Huzhou (CN); Yunhua Nie, Huzhou (CN); Jian Qiu, Huzhou (CN); Yumei Zhang, Huzhou (CN)

(73) Assignee: MICROVAST POWER SYSTEMS CO., LTD., Huzhou, Zhejiang Province (CN)

( * ) Notice: Subject to any disclaimer, the term of this patent is extended or adjusted under 35 U.S.C. 154(b) by 0 days.

(21) Appl. No.: 14/565,250

(22) Filed: Dec. 9, 2014

(65) Prior Publication Data

US 2015/0166587 A1 Jun. 18, 2015

(30) Foreign Application Priority Data

Dec. 13, 2013 (CN) .......................... 2013 1 0684970

(51) Int. Cl.
| | |
|---|---|
| *C07F 9/54* | (2006.01) |
| *C07F 9/6568* | (2006.01) |
| *H01M 10/0566* | (2010.01) |
| *H01M 10/0525* | (2010.01) |

(52) U.S. Cl.
CPC .............. *C07F 9/5407* (2013.01); *C07F 9/5442* (2013.01); *C07F 9/65688* (2013.01); *H01M 10/0525* (2013.01); *H01M 10/0566* (2013.01); *H01M 2300/0025* (2013.01); *Y02E 60/122* (2013.01)

(58) Field of Classification Search
CPC ............................. C07F 9/5407; C07F 9/5442
See application file for complete search history.

(56) References Cited

U.S. PATENT DOCUMENTS

| | | | | |
|---|---|---|---|---|
| 3,459,795 A | * | 8/1969 | Frank et al. .................... | 562/512 |
| 4,122,123 A | * | 10/1978 | Hestermann et al. ............. | 568/9 |
| 4,892,944 A | * | 1/1990 | Mori et al. .................... | 544/107 |
| 5,705,696 A | * | 1/1998 | King, Jr. ....................... | 564/296 |

FOREIGN PATENT DOCUMENTS

CN            1503778 A        6/2004

* cited by examiner

*Primary Examiner* — Brian J Davis
(74) *Attorney, Agent, or Firm* — Cheng-Ju Chiang

(57) ABSTRACT

A two-step pathway for preparing high pure quaternary phosphonium salts is disclosed. In the first step, hydrogen phosphide ($PH_3$) or a higher phosphine reacts with a protonic compound to produce a phosphonium salt, which then reacts with a carbonic acid diester to produce a quaternary phosphonium salt in the second step. On one hand, hydrogen phosphide ($PH_3$) and higher phosphines, including primary phosphines, secondary phosphines, and tertiary phosphines, after neutralization with protonic compound, become sufficiently reactive and can be alkylated by carbonic acid diester to form quaternary phosphonium cations. On the other hand, as an anion-exchange procedure is completely avoided, the process not only gives quaternary phosphonium salts of high purity, but also gives people freedom to design the cation and the anion of a quaternary phosphonium salt synchronously by choosing a preferred phosphine and a protonic compound that can supply a desired anion.

25 Claims, No Drawings

METHOD FOR PREPARING QUATERNARY PHOSPHONIUM SALTS

CROSS-REFERENCE TO RELATED APPLICATIONS

The present invention claims benefit from China Patent Application, which bears a serial No. CN201310684970.3 and filed on Dec. 13, 2013 and contents of which are incorporated herein for reference.

FIELD OF THE INVENTION

The present invention relates to a process for preparation of quaternary phosphonium salts of high purity.

BACKGROUND OF THE INVENTION

By variation of the four substituents on the phosphonium cation along with the available anions, we can obtain an enormous number of possible salts. Among them, the salts that melt below the normal boiling point of water, which are known as "ionic liquids (ILs)", have attracted extensive attention. In some applications where they are used as phase transfer catalysts in chemical synthesis, electrolytes in energy storage systems, including lithium ion batteries, solar cells, actuators, and supercapacitors, and additives in medicaments and water treatment, quaternary phosphonium based ILs show superior performance as compared to quaternary ammonium based ILs. However, quaternary phosphonium based ILs have been much less studied. The slow progress on quaternary phosphonium based ILs can be attributed to the difficulty in synthesizing their starting materials, for example phosphine derivatives, and further the process for preparation of them.

Generally, quaternary phosphonium salts are synthesized by reacting tertiary phosphines with alkyl halides, followed by an anion-exchange process if the anion other than halide ions ($X^-$) is desired.

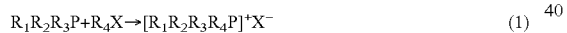  (1)

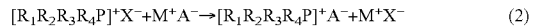  (2)

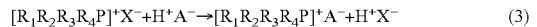  (3)

Alternatively, it is done by the addition of a metal salt $M^+[A]^-$ with precipitation of $M^+X^-$ or by displacement of the original ion by a strong acid MAI with release of $H^+X^-$. It deserves attention that those salts obtained by anion-exchange process are possibly contaminated with a small amount of $X^-$ ions unless the exchange reaction is fully completed.

As a synthesis process for a quaternary phosphonium salt with the anion of $SO_4^{2-}$, for example, a quaternary phosphonium chloride has to be prepared first as shown in equation (1), and further a reaction of the quaternary phosphonium chloride with sulfuric acid as shown in equation (3) is required. During the anion-exchange process, the reaction equilibrium is shifted to the right side by continuous removal of volatile hydrochloric acid. In another case of preparing a quaternary phosphonium salt with the anion of $BF_4^-$, a quaternary phosphonium chloride is prepared as shown in equation (1), and followed by a reaction of the quaternary phosphonium chloride with $NaBF_4$ in organic solvent such as acetone as shown in equation (2). When a silver salt is used instead of the alkali metal salt, the anion exchange reaction proceeds fast. In despite of the high cost, however, it is still difficult to obtain the desired quaternary phosphonium salt of high purity wherein the content of halide ion is very low.

On the other hand, the variation in properties between the quaternary phosphonium salts, even those with a same cation but different anions, is dramatic. The salts with anions such as $NO_3^-$, $CO_3^{2+}$, $PF_6^-$, $BF_4^-$, $C_2O_4^{2-}$, $Al_2Cl_7^-$, $CH_3COO^-$, $CF_3SO_3^-$, $C_4H_9SO_3^-$, $CF_3COO^-$, $N(CF_3SO_2)_2^-$, $N(C_2F_5SO_2)_2^-$, $N(C_4F_9SO_2)_2^-$, $N[(CF_3SO_2)(C_4F_9SO_2)]^-$, and $C(CF_3SO_2)_3^-$, etc., may exhibit lower melting point, higher electrical conductivity, lower viscosity and/or stronger hydrophobicity as compared to the quaternary phosphonium halides. This sort of variation in physical and/or chemical properties gives rise to wider application in green chemistry and as novel electrochemical materials in various electrochemical energy storage systems. It is of great significance, therefore, to develop a new process of preparing high pure quaternary phosphonium salts with different anions.

U.S. Pat. No. 4,892,944 discloses a process of preparing a quaternary phosphonium salt by reacting a tertiary phosphine with a carbonic acid diester to form a corresponding quaternary phosphonium carbonate and further mixing it with an acid to perform decarboxylaiton, as shown in equations below.

  (4)

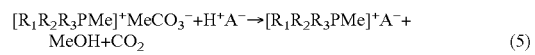  (5)

According to the process, numerous quaternary phosphonium salts having various anions can be efficiently produced. To some extent the contamination of the anions could be avoided because in the presence of acid the alkyl carbonate ion is readily transformed to alcohol and $CO_2$, which can be removed by simple method. However, this methodology is only applicable when tertiary phosphines are used as substrates. More readily available phosphine ($PH_3$) and other phophine derivatives, including primary phosphines ($RPH_2$) and secondary phosphines ($R_1R_2PH$), can not be alkylated by carbonic acid diester to give quaternary phosphonium compounds as shown in equation (4).

SUMMARY OF THE INVENTION

The present invention provides a two-step pathway for preparing high purity quaternary phosphonium salts. The process for preparing a quaternary phosphonium salt comprising: a) a first step of reacting hydrogen phosphide ($PH_3$) or a higher phosphine with a protonic compound to produce a phosphonium salt, and b) a second step of reacting the phosphonium salt obtained from the first step with a carbonic acid diester to produce a quaternary phosphonium salt. While the byproducts include alcohol and $CO_2$ are continually removed as the reaction proceeds or completely distilled off after the reaction.

As a great feature of this invention, apart from tertiary phosphines, various phosphines, including primary phosphines, secondary phosphines, and even hydrogen phosphide ($PH_3$) can be used as raw materials. That is, hydrogen phosphide ($PH_3$) and higher phosphines, after neutralization with protonic compound, become sufficiently reactive and could be alkylated by carbonic acid diester to form quaternary phosphonium cations.

The present invention, wherein the anion-exchange procedure is completely avoided, not only gives quaternary phosphonium salts of high purity, but also gives people freedom to design the cation and the anion of a quaternary phosphonium salt synchronously by choosing a preferred phosphine and a protonic compound that can supply a desired anion.

DETAILED DESCRIPTION OF THE INVENTION

As the phosphine which is a raw material in this invention, there are hydrogen phosphide ($PH_3$) and phosphine derivatives including primary phosphines ($RPH_2$), secondary phosphines ($R_1R_2PH$), and tertiary phosphines ($R_1R_2R_3P$). As the primary phosphine that is a raw material in this invention, there are methyl phosphine, ethyl phospine, n-propyl phosphine, cyclohexyl phosphine, and phenyl phosphine, etc. As the secondary phosphine that is a raw material in this invention, there are dimethyl phosphine, diethyl phosphine, di-i-propyl phosphine, diphenyl phosphine, di-i-butyl phosphine, dicyclohexyl phosphine, diphenyl phosphine, and ethyl methyl phosphine, etc. As the tertiary phosphine that is a raw material in this invention, there are trimethyl phosphine, triethyl phosphine, tripropyl phosphine, tri-i-butyl phosphine, tri-n-butyl phosphine, tri-n-pentyl phosphine, tricyclohexyl phosphine, tri-n-hexyl phosphine, tri-n-octyl phosphine, triphenyl phosphine, dimethyl phenyl phosphine, diethyl phenyl phosphine, butyl diphenyl phosphine, tribenzyl phosphine, tris(hydroxymethyl) phosphine, diethyl 2-chloroethyl phosphine, and tris(pentafluoroethyl) phosphine etc. As the phosphine derivative that is a raw material in this invention, there are cyclic phosphines such as 1-ethyl phosphoran, 1-phenyl phosphoran, 1-phenyl phosphane, and 1-phenyl phosphepane, etc.

In the present invention, the protonic compounds are the chemicals that can react with hydrogen phosphide ($PH_3$) or phosphine derivatives to form phosphonium salts. As the protonic compounds, there are inorganic acids including $HAlO_2$, $HAl(OH)_4$, $H_3AsO_4$, $HAsO_2$, $H_3AsO_3$, $H_4AS_2O$, $H_3BO_3$, $(HBO_2)_n$, $H_2B_4O_7$, $HBO_3$, $H_5BW_{12}O_{40}$, $HBrO_3$, $HBrO_2$, $HBrO$, $HBrO_4$, $H_4CO_4$, $H_2C_2O_6$, $H_2CO_4$ (or $H_2CO_3.H_2O_2$), $HClO_3$, $HClO_4$, $HClO_2$, $HClO$, $HONC$, $HOCN$, $HNCO$, $HIO_3$, $HIO$ (or $IOH$, $HIO_4$), $H_5IO_6$, $H_4I_2O_9$, $HNO_3$, $HNO_2$, $H_3PO_4$, $H_5PO_5$, $(HPO_3)n$, $H_3PO_3$, $H_4P_2O_5$, $HPO_2$, $H_3PO_2$, $H_4P_2O_6$, $H_4P_2O_7$, $H_2SO_4$, $H_2SO_3$, $H_2S_2O_3$, $H_2S_2O_7$, $H_2SO_2$, $H_2S_xO_6$ (x=2~6), $H_6SO_6$, $H_2S_2O_4$, $H_2SO_5$, $H_2S_2O_8$, $HSO_3Cl$, $HSO_3F$, $H_2SiO_3$ (or $SiO_2.H_2O$), $H_4SiO_4$, $H_2Si_2O_5$ (or $SiO_2.H_2O$), $H_4Si_3O_8$, $H_6Si_2O_7$ (or $2SiO_2.3H_2O$), $H[CHB_{11}Cl_{11}]$, $H_2S$, $H_2CS_4$, $H_2CS_3$, $HCN$, $HSeCN$, $HSCN$, $HBF_4$, $H_2SiF_6$, $HPF_6$, $HF$, $HCl$, $HBr$, and $HI$, etc. And there are organic acids including aliphatic monocarboxylic acids such as formic acid, acetic acid, propionic acid, butyric acid, valeric acid, caproic acid, enanthic acid, caprylic acid, pelargonic acid, capric acid, undecanic acid, lauric acid, tridecanic acid, myristic acid, pentacanic acid, palmitic acid, heptadecanic acid, stearic acid, nonadecanic acid, arachidic acid, isobutyric acid, isovaleric acid, isocaproi acid, ethyl butyric acid, methyl valeric acid, isocaprylic acid, propyl valeric acid, ethyl caproic acid, isocapric acid, tuberculostearic acid, pivalic acid, 2,2-dimethylbutani acid, 2,2-dimethylpentanic acid, 2,2-dimethylhexanic acid, 2,2-dimethylheptanic acid, 2,2-dimethyloctanic acid, 2-methyl-2-ethylbutanic acid, 2-methyl-2-ethylpentanic acid, 2-methyl-2-ethylhexanic acid, 2-methyl-2-ethyl-j eptanic acid, 2-methyl-2-propylpentanic acid, 2-methyl-2-propylhexanic acid, 2-methyl-2-propylheptanic acid, acrylic acid, crotonic acid, isocrotonic acid, 3-butenic acid, pentenic acid, hexenic acid, heptenic acid, octenic acid, nonenic acid, decenic acid, undecenic acid, dodecinic acid, tuzuic acid, physteric acid, goshuyuic acid, palmitoleic acid, petroselinic acid, oleic acid, elaidic acid, vaccenic acid, gadoleic acid, methacrylic acid, 3-methylcrotonic acid, tiglic acid, methyl pentenic acid, cyclopentacarboxylic acid, cyclohexanecarboxylic acid, trifluoroacetic acid, phenylacetic acid, chloroacetic acid, glycoric acid, lactic acid, etc.; aliphatic polycarboxylic acids such as citric acid, succinic acid, glutaric acid, adipic acid, pimelic acid, suberic acid, azelaic acid, sebacic acid, undecane diacid, dodecane diacid, tridecane diacid, tetradecane diacid, pentadecane diacid, hexadecane diacid, heptadecane diacid, octadecane diacid, noncadecane diacid, eicosane diacid, methyl malonic acid, ethyl malonic acid, propyl malonic acid, butyl malonic acid, hexyl malonic acid, dimethyl malonic acid, methyl ethyl malonic acid, diethylmalonic acid, methyl propyl malonic acid, methyl butyl malonic acid, ethyl propyl malonic acid, dipropyl malonic acid, ethyl butyl malonic acid, propyl butyl malonic acid, dibutylmalonic acid, methylsuccinic acid, ethylsuccinic acid, 2,2-dimethylsuccinic acid, 2,3-dimethylsuccinic acid, 2-methyl-glutaric acid, maleic acid, citraconic acid, itaconic acid, methyleneglutaric acid, monomethyl maleate, 1,5-octanedicarboxylic acid, 5,6-decanedicarboxylic acid, 1,7-decanedicarboxylic acid, 4,6-dimethyl-4-nonene-1,2-dicarboxylic acid, 4,6-dimethyl-1,2-nonanedicarboxylic acid, 1,7-dodecanedicarboxylic acid, 5-ethyl-1,10-decanedicarboxylic acid, 6-methyl-6-dodecene-1,12-dicatboxylic acid, 6-methyl-1,12-dodecanedicarboxylic acid, 6-ethylene-1,12-dodecanedicarboxylic acid, 7-methyl-7-tetradecene-1,14-dicarboxylic acid, 7-methyl-1,14-tetradecanedicarboxylic acid, 3-hexyl-4-decene-1,2-dicarboxylic acid, 3-hexyl-1,12-decanedicarboxylic acid, 6-ethylene-9-hexadecene-1,16-dicarboxylic acid, 6-ethyl-1,16-hexadecanedicarboxylic acid, 6-phenyl-1,12-dodecanedicarboxylic acid, 7,12-dimethyl-7,11-octadecanediene-1,18-dicarboxylic acid, 7,12-dimethyl-1,18-octadecanedicarboxylic acid, 6,8-diphenyl-1,14-tetradecanedicarboxylic acid, 1,1-cyclopen-tanedicarboxylic acid, 1,1-cyclopentanedicarboxylic acid, 1,2-cyclopentanedicarboxylic acid, 1,1-cyclohexanedicarboxylic acid, 1,2-cyclohexanedicarboxylic acid, 4-cyclohexene-1,2-dicarboxylic acid, 5-nobor-nene-2,3-dicarboxylic acid, malic acid, glutamic acid, tartaric acid, citric acid, etc.; aromatic monocarboxylic acids (including o-, m-, and p-isomers) such as benzoic acid, toluic acid, ethylbenzoic acid, propylbenzoic acid, isopropylbenzoic acid, butylbenzoic acid, sec-butylbenzoic acid, tert-butylbenzoic acid, hydroxybenzoic acid, anisic acid, ethoxybenzoic acid, propoxybenzoic acid, isopropoxybenzoic acid, butoxybenzoic acid, isobutoxybenzoic acid, sec-butoxybenzoic acid, tert-butoxybenzoic acid, aminobenzoic acid, N-methylaminobenzoic acid, N-ethylaminobenzoic acid, N-propylaminobenzoic acid, N-isopropylaminobenzoic acid, N-butylaminobenzoic acid, N-isobutylaminobenzoic acid, N-sec-butylaminobenzoic acid, N-tert-butylaminobenzoic acid, N,N-dimethylaminobenzoic acid, N,N-diezoic acid, resorcinic acid; aromatic polycarboxylicthalic acid such as nitrophthalic acid, trimellitic acid, hemimellitic acid, trimesic acid, and pyromellitic acid, etc.

Also, the protonic compounds in the present invention include the compounds that are far more than the traditional acids. As the non-acid protonic compounds in this invention, there are compounds having at least one proton activated by the neighboring groups that are electron-withdrawing. Those compounds become "acidic" enough to perform the neutralization reaction with basic hydrogen phosphide ($PH_3$) and/or phosphine derivatives. The non-acid protonic compounds can be selected from phenols such as phenol, p-fluorophenol, β-naphthol, o-nitrophenol, p-nitrophenol, p-aminophenol, catechol, 2,4-dichlorophenol, and 4,4'-dihydroxydiphenyl-2,2-propane, etc. Also, as the non-acid protonic compounds, there are such as $HN(C_mF_{2m+1}SO_2)(C_nF_{2n+1}SO_2)$, $HN(C_nF_{2n+1}SO_2)_2$, and $HNC_mF_{2m}SO_2$, etc., wherein m, n are integral numbers of from 1 to 10, and preferably from 1 to 5. Specific examples of the protonic compound are shown as follows:

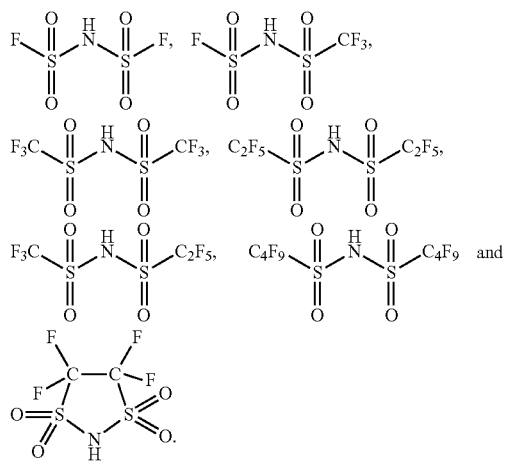

In the present invention, the non-acid protonic compounds can also be tri(trifluoromethylsulfonyl) methane, tri(pentafluoroethylsulfonyl) methane, or tri(nonfluorobutylsulfonyl) methane, etc.

In the first step of this invention, wherein the neutralization reaction of a hydrogen phosphide ($PH_3$) or a higher phosphine and a protonic compound occurs in the presence or absence of a solvent, the molar ratio of the starting materials varies with the proton quantity that the protonic compound can supply. In the case of using a protonic compound with one active proton, the neutralization reaction is preferably performed using a phosphine and the protonic compound in a molar ratio of 1. As one specific example, hydrogen phosphide ($PH_3$) reacts with hydrofluoric acid (HF) in a molar ratio of 1 to give a stoichiometric amount of the phosphonium salt ($PH_4F$). In the case of using a protonic compound with two or more active protons, the neutralization reaction could be performed using a phosphine and the protonic compound in a molar ratio of 1, 2, or 3. For instance, triethyl phosphine reacts with phosphoric acid ($H_3PO_4$) in a molar ratio of 1 to form the phosphonium salt ($[(C_2H_5)_3PH_1][H_2PO_4]$), whereas triethyl phosphine reacts with phosphoric acid ($H_3PO_4$) in a molar ratio of 2 or 3 to form the phosphonium salts of $[(C_2H_5)_3PH]_2[HPO_4]$ and $[(C_2H_5)_3PH]_3[PO_4]$, respectively. A little excessive amount of either of the starting materials, in particular, the one that is more available and can be easily removed from the system, is usually added in order to perform the reaction completely.

The inorganic acids are usually aqueous solutions, such as sulfuric acid, nitric acid, hydrochloric acid, hydrobromic acid, hydrofluoric acid, phosphoric acid, hexafluorophosphoric acid, and fluoroboric acid, etc. When those acids are used in the neutralization reaction, extra solvent may be not needed. If organic acids or other protonic compounds other than traditional acids such as acetic acid, propionic acid, benzoic acid, and various imines, etc., are used, solvents such as alcohols, ethers, esters, alkanes, toluene, dichloroethane, trichloromethane, tetrahydrofuran and methylbenzene, etc., are preferably added.

Properties of quaternary phosphonium salts can be adjusted by choosing various protonic compounds with different anions such as $F^-$, $NO_3^-$, $CO_3^{2-}$, $PF_6^-$, $BF_4^-$, $C_2O_4^{2-}$, $SO_4^{2-}$, $PO_4^{3-}$, $Al_2Cl_7^-$, $CH_3COO^-$, $CF_3SO_3^-$, $C_4H_9SO_3^-$, $CF_3COO^-$, $N(CF_3SO_2)_2^-$, $N(C_2F_5SO_2)_2^-$, $N(C_4F_9SO_2)_2^-$, $N[(CF_3SO_2)(C_4F_9SO_2)]^-$, and $C(CF_3SO_2)_3^-$ et al. By varying the molar ratio of phosphine and protonic compound, which has two or more protons, a quaternary phosphonium salt with a common cation but a different anion can also be obtained.

The neutralization reaction usually occurs at temperature of from −20° C. to 80° C., preferably from 0° C. to 60° C. If the reaction is strongly exothermic, it is better to slow down the feeding speed of the raw materials or decrease the reaction temperature by cooling. There is no particular restriction on the reaction pressure. The pressure is usually from 0.05 MPa to 2 MPa, preperably from 0.09 MPa to 0.5 MPa, more preferably from 0.095 MPa to 0.12 MPa. The reaction takes from several minutes to several hours, usually from one half hour to 12 hours, more usually from 2 hour to 8 hours. As the neutralization reaction generally undergoes fast, the starting materials, including both the phosphines and the protonic compounds, could be sufficiently converted into corresponding phosphonium salts. By distilling off the unreacted starting materials and the solvent, in the case of using a solvent, or if necessary, by recrystallization from a suitable solvent, the product with high purity can be obtained and then sent to the second step for quaternization reaction. In the cases, wherein the unreacted materials and/or solvent have no harmful effects on the quaternization reaction, the product can go directly to the second step without any treatment.

In the second step of this invention, the phosphonium salt obtained from the first step reacts with a carbonic acid diester in the presence or absence of solvent to produce a quaternary phosphonium salt. As the carbonic acid diester, there are linear carbonates such as dimethyl carbonate, diethyl carbonate, dipropyl carbonate, ethyl methyl carbonate, di(trifluoroethyl) carbonate, and dibenzyl carbonate, etc., and cyclic carbonates such as ethylene carbonate, propylene carbonate, and fluoroethylene carbonate, etc. There is no particular restriction on the carbonic acid diester being used. However, a carbonic acid diester with an alkyl or a substituted alkyl moiety of small carbon atom number such as dimethyl carbonate and ethylene carbonate is preferred.

The molar ratio of a phosphonium salt and a carbonic acid diester varies with the proton quantity on the phosphonium cation. In the case of using hydrogen phosphide ($PH_3$) as starting material, there are four protons on the phosphonium cation after the neutralization reaction in the first step. The phosphonium salt reacts with a carbonic acid diester in a molar ratio of 4 to give a quaternary phosphonium salt in the second step. The reactions are shown by the following equation (6) and equation (7):

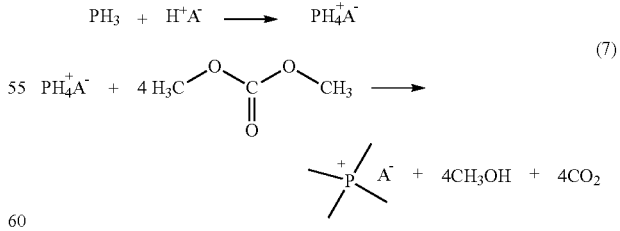

wherein HA represents a protonic compound, and $A^-$ represents a conjugated base thereof.

When a primary phosphine ($R_1PH_2$) is used as starting material, the quaternization reaction occurs using the phosphonium salt and a carbonic acid diester in a molar ratio of 3, as shown by the following equations:

(8)

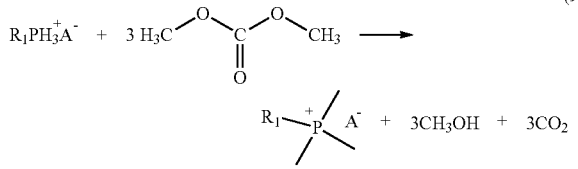

(9)

wherein $R_1$ represents a substituent group of the primary phosphine.

When a secondary phosphine ($R_1R_2PH$) is used as starting material, the quaternization reaction occurs using the phosphonium salt and a carbonic acid diester in a molar ratio of 2, as shown by the following equations:

(10)

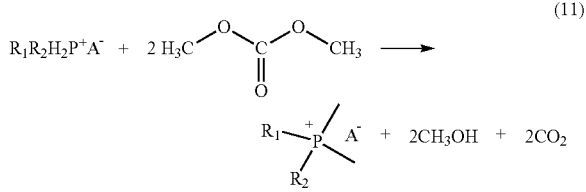

(11)

wherein $R_1$ and $R_2$ represent substituent groups of the secondary phosphine.

When a tertiary phosphine ($R_1R_2R_3P$) is used as starting material, the quaternization reaction occurs using the phosphonium salt and a carbonic acid diester in a molar ratio of 1, as shown by the following equations:

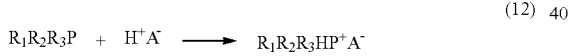

(12)

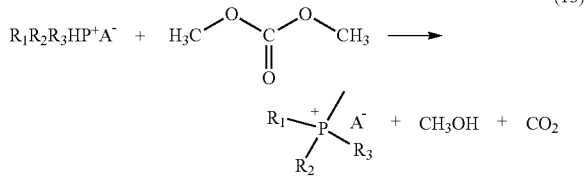

(13)

wherein $R_1$, $R_2$ and $R_3$ represent substituent groups of the tertiary phosphine.

Usually, a little excessive amount of a carbonic acid diester is added in the quaternization step in order to sufficiently convert the phosphonium salt obtained from the first step. Carbonic acid diester can also be used in a great quantity, wherein it may serve as the solvent. In the case wherein solvents are considered necessary, solvents such as alcohols, aethers, esters, alkanes, toluene, dichloroethane, trichloromethane, tetrahydrofuran, and methylbenzene, etc., and their mixtures, are preferably added. Replacing air inside the reactor by inert gas, or removing air by vacuuming prior to the reaction, is preferable to avoid the side effects of air on the reaction. The quaternization reaction usually occurs at temperature of from 20° C. to 280° C., preferably from 100° C. to 200° C. When the reaction undergoes, the reaction pressure usually goes up, ranging from close to 0 to about 3 MPa. During the reaction, by continuously removing carbon dioxide generated can decrease the pressure. Slowing down the feeding speed of carbonic acid diester is also an effective way to control the pressure. It is preferred that the pressure is varied within 0.8 MPa to about 2 MPa. The reaction time usually ranges from 0.5 hours to 24 hours, more usually from 2 hours to 15 hours. After the reaction is finished, the unreacted materials, the by-produced alcohols and, if a solvent is used, the solvent are distilled off to achieve a desired quaternary phosphonium salt. If necessary, by proper treatments such as recrystallization, the high purity product can be obtained. By choosing different phosphines and carbonic acid diesters, tone can obtain various quaternary phosphonium cations by this invention. Specific examples are shown below:

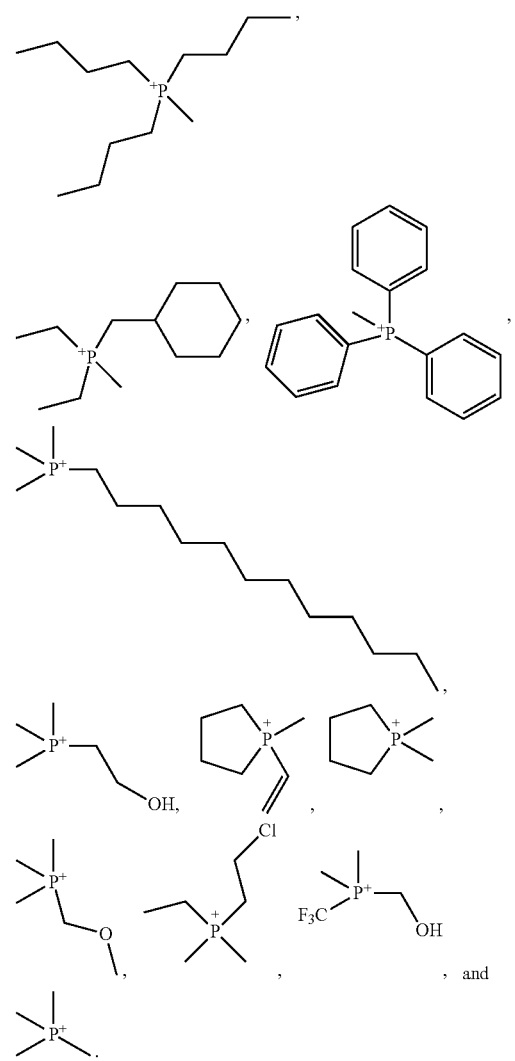

As described above, the present invention provides a neat method for preparing high purity quaternary phosphonium salts with a diversity of structures. Various anions can be easily introduced into the quaternary phosphonium salts by choosing desired protonic compounds, and the four substituent groups on the cations can be varied by using various phosphines and various carbonic acid diesters. As the large feature of this invention, a great number of phosphines including hydrogen phosphide, primary phosphines, secondary phosphines, and tertiary phosphines, can be used as starting materials, and efficiently converted to quaternary phosphonium cations.

Various quaternary phosphonium based ILs can be synthesized by the process of the present invention, which obviously provides electrolytes that may be applied in electrochemical energy storage systems such as batteries, fuel cells, solar cells, and supercapacitors. Also, the present invention may provide some solutions to biotechnology, biofuel processing, and water treatment, etc., wherein quaternary phosphonium salts are applicable.

DESCRIPTION OF EMBODIMENTS OF THE INVENTION

The detailed descriptions of the present invention set forth below in connection with the examples are preferred embodiments of the present invention, but the present invention is not limited to the embodiments and forms described hereinafter.

Example 1

In a reactor wherein air was replaced by $N_2$, 260.0 g (2.6 mol) of hydrochloric acid (36 wt %) was added and cooled to 5° C. by a ice-bath. 300.0 g (2.5 mol) of triethylphosphine was then added dropwise under strong stirring, and a proper quantity of methanol was added to dilute the reaction mixture. After a half hour of reaction, the reaction temperature was increased to about 60° C., and the unreacted materials as well as the solvents, including water and methanol, were removed by distillation under vacuum to obtain triethylphosphonium chloride.

The obtained triethylphosphonium chloride was transferred to an autoclave, wherein air was removed prior to heating. When the temperature increased to 140° C., a mixture comprising 100 g of methanol and 500 g of dimethyl carbonate was fed into the autoclave. By adjusting the feeding speed, the reaction pressure was varied within the range of from 1.3 MPa to 1.5 MPa. When the pressure was higher, $CO_2$ was continuously removed from the reaction system. After feeding, the reaction temperature was further increased to about 150° C., and the reaction pressure went up slowly to from 1.6 MPa to 1.8 MPa. The reaction was performed for 2 more hours at this temperature and pressure. After about 8 hours of reaction, the autoclave was cooled and the crude product was obtained after distilling off the unreacted materials and solvents. 419.0 g of methyl triethyl phosphonium chloride was achieved after drying at 45° C. and 0.1 kPa for 8 hours.

Example 2

In an reactor wherein air was replaced by $N_2$, 300.0 g (1.5 mol) of tributyl phosphine and 1000 mL of methanol were added and cooled to about 0° C. by a ice-bath. 427.6 g (1.5 mol) of trifluoromethanesulfonimide was then added dropwise under strong stirring, and 202.0 g (2.2 mol) of dimethyl carbonate was also added afterwards. After one hour of reaction and mixing, the reaction mixture was transferred to an autoclave, wherein air was removed prior to heating. After 6 hours of reaction at temperature of 180° C. and pressure of from 1.6 MPa to 1.7 MPa, the crude product was obtained after distilling off the unreacted materials and solvent. 705.7 g of methyl tributyl phosphonium bis(trifluoromethanesulfonyl)amide was obtained after washing and drying at 60° C. and 0.1 kPa for 4 hours.

Example 3

In a reactor wherein air was replaced by $N_2$, 300.0 g of (1.1 mol) triphenyl phosphine and 500 mL of methanol were added and cooled to 10° C. by a ice-bath. 321.8 g (1.1 mol) of trifluoromethanesulfonimide was then added dropwise under strong stirring, and 202.0 g (2.2 mol) of dimethyl carbonate was also added afterwards. After one hour of reaction and mixing, the reaction mixture was transferred to an autoclave, wherein air was removed prior to heating. After 4 hours of reaction at temperature of 160° C. and at pressure of from 1.4 MPa to 1.5 MPa, the crude product was obtained after distilling off the unreacted materials and solvent. 584.8 g of methyl triphenyl phosphonium bis(trifluoromethanesulfonyl)amide was obtained after recrystallization and drying at 60° C. and 0.1 kPa for 4 hours.

Example 4

In a reactor wherein air was replaced by $N_2$, 300.0 g of (1.1 mol) triphenyl phosphine and 500 mL of methanol were added and cooled to 10° C. by a ice-bath. 250.8 g (1.1 mol) of fluoroboric acid aqueous solution (40 wt %) was then added dropwise under strong stirring. After one hour of reaction, the reaction temperature was increased to about 50° C., and the unreacted materials as well as the solvents, including water and methanol, were removed by distillation under vacuum to obtain triphenylphosphonium tetrafluoroborate. The phosphonium salt was then transferred to an autoclave, and 202.0 g (2.2 mol) of dimethyl carbonate was also introduced. After 6 hours of reaction at temperature of 160° C. and at pressure of from 1.4 MPa to 1.5 MPa, the crude product was obtained after distilling off the unreacted materials and solvent. 375.0 g of methyl triphenyl phosphonium tetrafluoroborate was obtained after washing and drying at 60° C. and 0.1 kPa for 4 hours.

Example 5

In a reactor wherein air was replaced by $N_2$, 400.0 g (2.2 mol) of diphenyl phosphine and 400 mL of methanol were added and cooled to 10° C. by a ice-bath. 604.3 g (2.2 mol) of trifluoromethanesulfonimide was then added dropwise under strong stirring. After one hour of reaction, the reaction temperature was increased to about 60° C., and the unreacted materials as well as the solvents were removed by distillation under vacuum to obtain diphenyl phosphonium bis(trifluoromethanesulfonyl)amide.

The diphenyl phosphonium bis(trifluoromethanesulfonyl) amide was transferred to an autoclave, wherein air was removed prior to heating. When the temperature increased to 130° C., a mixture comprising 300 g of methanol and 500 g of dimethyl carbonate was fed into the autoclave. By adjusting the feeding speed, the reaction pressure was varied within the range of from 1.0 MPa to 1.4 MPa. When the pressure was higher, $CO_2$ was continually removed from the reaction system. After feeding, the reaction temperature was further increased to about 150° C., and the reaction pressure went up slowly to from 1.4 MPa to 1.5 MPa. The reaction was performed for another 4 hours at the temperature and pressure. After about 8 hours of reaction in all, the autoclave was cooled and the crude product was obtained after distilling off the unreacted materials and solvent. 1009.8 g of dimethyl diphenyl phosphonium bis(trifluoromethanesulfonyl)amide was given after recrystallization and drying at 45° C. and 0.1 kPa for 8 hours.

Example 6

In a reactor wherein air was replaced by $N_2$, 200.0 g of (1.2 mol) diethylphenyl phosphine and 400 mL of methanol were added and cooled to 15° C. by a ice-bath. 338.6 g (1.2 mol) of trifluoromethanesulfonimide was then added dropwise under strong stirring, and 202.0 g (2.2 mol) of dimethyl carbonate was also added after the reaction was complete. The reaction mixture was transferred to an autoclave, wherein air was removed prior to heating. After 2 hours of reaction at temperature of 180° C. and at pressure of from 1.2 MPa to 1.5 MPa, the crude product was obtained after distilling off the unreacted materials and solvent. 507.1 g of diethyl methyl phenyl phosphonium bis(trifluoromethanesulfonyl)amide was obtained after washing and drying at 60° C. and 0.1 kPa for 4 hours.

Example 7

In a reactor wherein air was replaced by $N_2$, 200.0 g of (1.1 mol) diphenyl phosphine and 400 mL of methanol were added and cooled to 10° C. by a ice-bath. 71.3 g (1.2 mol) of acetic acid was then added dropwise under strong stirring, and 202.0 g (2.2 mol) of dimethyl carbonate was also added after 5 hours of reaction. The reaction mixture was transferred to an autoclave, wherein air was removed prior to heating. After 6 hours of reaction at temperature of 170° C. and at pressure of from 1.4 MPa to 1.7 MPa, the crude product was obtained after distilling off the unreacted materials and solvent. 279.8 g of dimethyl diphenyl phosphonium acetate was obtained after washing and drying at 60° C. and 0.1 kPa for 4 hours.

Example 8

In a reactor wherein air was replaced by $N_2$, 300.0 g of (1.1 mol) triphenyl phosphine and 500 mL of methanol were added and cooled to 10° C. by a ice-bath. 320.3 g (1.14 mol) of trifluoromethanesulfonimide was then added dropwise under strong stirring, and 264.3 g (2.2 mol) of diethyl carbonate was also added after 1 hour of reaction. The reaction mixture was transferred to an autoclave, wherein air was removed prior to heating. After 2 hours of reaction at temperature of 180° C. and at pressure of from 1.4 MPa to 1.5 MPa, the crude product was obtained after distilling off the unreacted materials and solvent. 599.5 g of ethyl triphenyl phosphonium bis(trifluoromethyl sulfonyl) amide was obtained after washing and drying at 60° C. and 0.1 kPa for 4 hours.

Example 9

In a reactor wherein air was replaced by $N_2$, 520.0 g (5.2 mol) of hydrochloric acid (36 wt %) was added and cooled to 0° C. by a ice-bath. 180.2 g (5.3 mol) of hydrogen phosphide was then fed into the reactor under strong stirring, and a proper quantity of methanol was added to dilute the reaction mixture. After 10 hours of reaction, the reaction temperature was increased to about 45° C., and the unreacted materials as well as the solvents, including water and methanol, were removed by distillation under vacuum to obtain phosphonium chloride.

The obtained phosphonium chloride was transferred to an autoclave, wherein air was removed prior to feeding. 500 g of methanol was injected into the autoclave, and then the reaction temperature was increased to 180° C. By adjusting the feeding speed of dimethyl carbonate, the reaction pressure was varied within the range of from 1.3 MPa to 1.8 MPa. When the pressure was higher, $CO_2$ was continually removed from the reaction system. After feeding 2052 g (22.8 mol) of dimethyl carbonate in all, the reaction temperature was decreased to 150° C. and the reaction was performed for another 2 hours at the temperature and pressure. After the reaction was complete, the crude product was obtained by distilling off the unreacted materials and solvent. 619.8 g of tetramethyl phosphonium chloride was given after recrystallization and drying at 45° C. and 0.1 kPa for 8 hours.

Example 10

In a reactor wherein air was replaced by $N_2$, 300.0 g of (1.1 mol) triphenyl phosphine and 500 mL of methanol were added and heated to 60° C. 321.8 g (1.1 mol) of trifluoromethanesulfonimide was then added dropwise under strong stirring, and 176.0 g (2.0 mol) of ethylene carbonate was also added after a half hour of reaction. The reaction mixture was transferred to an autoclave, wherein air was removed prior to heating. After 4 hours of reaction at temperature of 160° C. and at pressure of from 1.4 MPa to 1.5 MPa, the crude product was obtained after distilling off the unreacted materials and solvent. 616.3 g of 2-hydroxyethyl triphenyl phosphonium bis(trifluoromethyl sulfonyl) amide was obtained after washing and drying at 60° C. and 0.1 kPa for 4 hours.

The invention claimed is:

1. A process for preparing a quaternary phosphonium salt comprising:
    (a) a first step of reacting hydrogen phosphide or a higher phosphine with a protonic compound to produce a phosphonium salt, and
    (b) a second step of reacting the phosphonium salt obtained from the first step with a carbonic acid diester to produce a quaternary phosphonium salt.

2. The process as claimed in claim 1, wherein the phosphine is selected from the group consisting of primary phosphines, secondary phosphines, and tertiary phosphines.

3. The process as claimed in claim 2, wherein the phosphine is selected from the group consisting of methyl phosphine, ethyl phospine, n-propyl phosphine, cyclohexyl phosphine, phenyl phosphine, dimethyl phosphine, diethyl phosphine, di-i-propyl phosphine, diphenyl phosphine, di-i-butyl phosphine, dicyclohexyl phosphine, diphenyl phosphine, ethyl methyl phosphine, trimethyl phosphine, triethyl phosphine, tripropyl phosphine, tri-i-butyl phosphine, tri-n-butyl phosphine, tri-n-pentyl phosphine, tricyclohexyl phosphine, tri-n-hexyl phosphine, tri-n-octyl phosphine, triphenyl phosphine, dimethyl phenyl phosphine, diethyl phenyl phosphine, butyl diphenyl phosphine, tribenzyl phosphine, tris(hydroxymethyl) phosphine, diethyl 2-chloroethyl phosphine, tris(pentafluoroethyl) phosphine, 1-ethyl phosphoran, 1-phenyl phosphoran, 1-phenyl phosphane, and 1-phenyl phosphepane.

4. The process as claimed in claim 1, wherein the protonic compound is selected from a group of inorganic acids.

5. The process as claimed in claim 4, wherein the protonic compound is selected from a group consisting of $HAlO_2$, $HAl(OH)_4$, $H_3AsO_4$, $HAsO_2$, $H_3AsO_3$, $H_4As_2O_7$, $H_3BO_3$, $(HBO_2)_n$, $H_2B_4O_7$, $HBO_3$, $H_5BW_{12}O_{40}$, $HBrO_3$, $HBrO_2$, $HBrO$, $HBrO_4$, $H_4CO_4$, $H_2C_2O_6$, $H_2CO_4$ (or $H_2CO_3 \cdot H_2O_2$), $HClO_3$, $HClO_4$, $HClO_2$, $HClO$, $HONC$, $HOCN$, $HNCO$, $HIO_3$, $HIO$ (or $IOH$, $HIO_4$), $H_5IO_6$, $H_4I_2O_9$, $HNO_3$, $HNO_2$, $H_3PO_4$, $H_5PO_5$, $(HPO_3)n$, $H_3PO_3$, $H_4P_2O_5$, $HPO_2$, $H_3PO_2$, $H_4P_2O_6$, $H_4P_2O_7$, $H_2SO_4$, $H_2SO_3$, $H_2S_2O_3$, $H_2S_2O_7$, $H_2SO_2$, $H_2S_xO_6$ (x=2~6), $H_6SO_6$, $H_2S_2O_4$, $H_2SO_5$, $H_2S_2O_8$, $HSO_3Cl$, $HSO_3F$, $H_2SiO_3$ (or $SiO_2 \cdot H_2O$), $H_4SiO_4$, $H_2Si_2O_5$ (or SiO$_2$.H$_2$O), H$_4$Si$_3$O$_8$, H$_6$Si$_2$O$_7$ (or 2SiO$_2$.3H$_2$O), H[CHB$_{11}$Cl$_{11}$], H$_2$S, H$_2$CS$_4$, H$_2$CS$_3$, HCN, HSeCN, HSCN, HBF$_4$, H$_2$SiF$_6$, HPF$_6$, HF, HCl, HBr, and HI.

6. The process as claimed in claim 1, wherein the protonic compound is selected from a group of organic acids.

7. The process as claimed in claim 6, wherein the protonic compound is selected from a group consisting of formic acid, acetic acid, propionic acid, butyric acid, valeric acid, caproic acid, enanthic acid, caprylic acid, pelargonic acid, capric acid, undecanic acid, lauric acid, tridecanic acid, myristic acid, pentacanic acid, palmitic acid, heptadecanic acid, stearic acid, nonadecanic acid, arachidic acid, isobutyric acid, isovaleric acid, isocaproi acid, ethyl butyric acid, methyl valeric acid, isocaprylic acid, propyl valeric acid, ethyl caproic acid, isocapric acid, tuberculostearic acid, pivalic acid, 2,2-dimethylbutani acid, 2,2-dimethylpentanic acid, 2,2-dimethylhexanic acid, 2,2-dimethylheptanic acid, 2,2-dimethyloctanic acid, 2-methyl-2-ethylbutanic acid, 2-methyl-2-ethylpentanic acid, 2-methyl-2-ethylhexanic acid, 2-methyl-2-ethyl-jeptanic acid, 2-methyl-2-propylpentanic acid, 2-methyl-2-propylhexanic acid, 2-methyl-2-propylheptanic acid, acrylic acid, crotonic acid, isocrotonic acid, 3-butenic acid, pentenic acid, hexenic acid, heptenic acid, octenic acid, nonenic acid, decenic acid, undecenic acid, dodecinic acid, tuzuic acid, physteric acid, goshuyuic acid, palmitoleic acid, petroselinic acid, oleic acid, elaidic acid, vaccenic acid, gadoleic acid, methacrylic acid, 3-methylcrotonic acid, tiglic acid, methyl pentenic acid, cyclopentacarboxylic acid, cyclohexanecarboxylic acid, trifluoroacetic acid, phenylacetic acid, chloroacetic acid, glycoric acid, lactic acid, citric acid, succinic acid, glutaric acid, adipic acid, pimelic acid, suberic acid, azelaic acid, sebacic acid, undecane diacid, dodecane diacid, tridecane diacid, tetradecane diacid, pentadecane diacid, hexadecane diacid, heptadecane diacid, octadecane diacid, noncadecane diacid, eicosane diacid, methyl malonic acid, ethyl malonic acid, propyl malonic acid, butyl malonic acid, hexyl malonic acid, dimethyl malonic acid, methyl ethyl malonic acid, diethylmalonic acid, methyl propyl malonic acid, methyl butyl malonic acid, ethyl propyl malonic acid, dipropyl malonic acid, ethyl butyl malonic acid, propyl butyl malonic acid, dibutylmalonic acid, methylsuccinic acid, ethylsuccinic acid, 2,2-dimethylsuccinic acid, 2,3-dimethylsuccinic acid, 2-methyl-glutaric acid, maleic acid, citraconic acid, itaconic acid, methyleneglutaric acid, monomethyl maleate, 1,5-octanedicarboxylic acid, 5,6-decanedicarboxylic acid, 1,7-decanedicarboxylic acid, 4,6-dimethyl-4-nonene-1,2-dicarboxylic acid, 4,6-dimethyl-1,2-nonanedicarboxylic acid, 1,7-dodecanedicarboxylic acid, 5-ethyl-1,10-decanedicarboxylic acid, 6-methyl-6-dodecene-1,12-dicatboxylic acid, 6-methyl-1,12-dodecanedicarboxylic acid, 6-ethylene-1,12-dodecanedicarboxylic acid, 7-methyl-7-tetradecene-1,14-dicarboxylic acid, 7-methyl-1,14-tetradecanedicarboxylic acid, 3-hexyl-4-decene-1,2-dicarboxylic acid, 3-hexyl-1,12-decanedicarboxylic acid, 6-ethylene-9-hexadecene-1,16-dicarboxylic acid, 6-ethyl-1,16-hexadecanedicarboxylic acid, 6-phenyl-1,12-dodecanedicarboxylic acid, 7,12-dimethyl-7,11-octadecanediene-1,18-dicarboxylic acid, 7,12-dimethyl-1,18-octadecanedicarboxylic acid, 6,8-diphenyl-1,14-tetradecanedicarboxylic acid, 1,1-cyclopen-tanedicarboxylic acid, 1,1-cyclopentanedicarboxylic acid, 1,2-cyclopentanedicarboxylic acid, 1,1-cyclohexanedicarboxylic acid, 1,2-cyclohexanedicarboxylic acid, 4-cyclohexene-1,2-dicarboxylic acid, 5-nobor-nene-2,3-dicarboxylic acid, malic acid, glutamic acid, tartaric acid, citric acid, benzoic acid, toluic acid, ethylbenzoic acid, propylbenzoic acid, isopropylbenzoic acid, butylbenzoic acid, sec-butylbenzoic acid, tert-butylbenzoic acid, hydroxybenzoic acid, anisic acid, ethoxybenzoic acid, propoxybenzoic acid, isopropoxybenzoic acid, butoxybenzoic acid, isobutoxybenzoic acid, sec-butoxybenzoic acid, tert-butoxybenzoic acid, aminobenzoic acid, N-methylaminobenzoic acid, N-ethylaminobenzoic acid, N-propylaminobenzoic acid, N-isopropylaminobenzoic acid, N-butylaminobenzoic acid, N-isobutylaminobenzoic acid, N-sec-butylaminobenzoic acid, N-tert-butylaminobenzoic acid, N,N-dimethylaminobenzoic acid, N,N-diezoic acid, resorcinic acid, nitrophthalic acid, trimellitic acid, hemimellitic acid, trimesic acid, and pyromellitic acid.

8. The process as claimed in claim 1, wherein the protonic compound is selected from a group of non-acid protonic compounds having at least one proton activated by the neighboring groups that are electron-withdrawing.

9. The process as claimed in claim 8, wherein the protonic compound is selected from a group of phenol, p-fluorophenol, β-naphthol, o-nitrophenol, p-nitrophenol, p-aminophenol, catechol, 2,4-dichlorophenol, and 4,4'-dihydroxydiphenyl-2,2-propane.

10. The process as claimed in claim 8, wherein the protonic compound is selected from a group of HN(C$_m$F$_{2m+1}$SO$_2$)(C$_n$F$_{2n+1}$SO$_2$), HN(C$_n$F$_{2n+1}$SO$_2$)$_2$, and HNC$_m$F$_{2m}$SO$_2$, wherein m, n are integral numbers of from 1 to 10.

11. The process as claimed in claim 10, wherein the protonic compound is selected from a group of

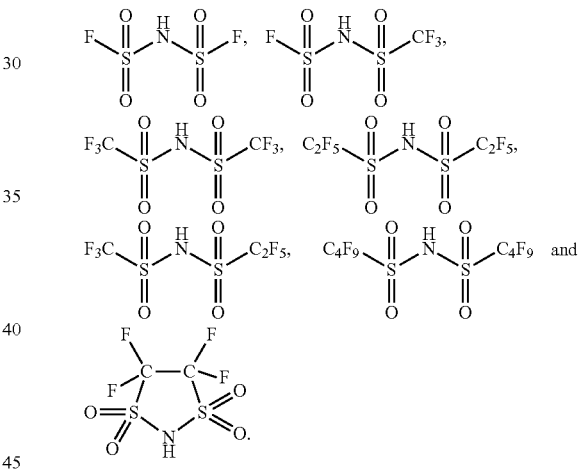

12. The process as claimed in claim 8, wherein the protonic compound is selected from a group consisting of tri(trifluoromethylsulfonyl) methane, tri(pentafluoroethylsulfonyl) methane, and tri(nonfluorobutylsulfonyl) methane.

13. The process as claimed in claim 1, wherein the reaction of step (a) occurs at temperature of from about −20° C. to 80° C.

14. The process as claimed in claim 13, wherein the reaction of step (a) occurs at temperature of from about 0° C. to 60° C.

15. The process as claimed in claim 1, wherein the reaction time of step (a) varies from one hour to 8 hours.

16. The process as claimed in claim 1, wherein the carbonic acid diester is selected from a group consisting of dimethyl carbonate, diethyl carbonate, dipropyl carbonate, ethyl methyl carbonate, di(trifluoroethyl) carbonate, dibenzyl carbonate, ethylene carbonate, propylene carbonate, and fluoroethylene carbonate.

17. The process as claimed in claim 1, wherein the reaction of step (b) occurs at temperature of from about 20° C. to 280° C.

18. The process as claimed in claim 17, wherein the reaction of step (b) occurs at temperature of from about 100° C. to 200° C.

19. The process as claimed in claim 1, wherein the reaction of step (b) occurs at pressure of from about 0.1 MPa to 3 Mpa.

20. The process as claimed in claim 19, wherein the reaction of step (b) occurs at pressure of from about 0.8 MPa to 2 Mpa.

21. The process as claimed in claim 20, wherein the reaction pressure of step (b) is adjusted by continuously removing carbon dioxide generated or varying the feeding speed of carbonic acid diester.

22. The process as claimed in claim 1, wherein the reaction time of step (b) varies from about 0.5 hours to 24 hours.

23. The process as claimed in claim 22, wherein the reaction time of step (b) varies from about 2 hours to 15 hours.

24. An electrolyte for electrochemical energy storage systems comprising the quaternary phosphonium salt prepared by the process of claim 1.

25. A secondary lithium ion battery comprising the electrolyte of claim 24.

\* \* \* \* \*